(12) United States Patent
Robinson

(10) Patent No.: US 8,603,143 B2
(45) Date of Patent: Dec. 10, 2013

(54) SPINOUS PROCESS FIXATION APPARATUS

(76) Inventor: James C. Robinson, Atlanta, GA (US)

( * ) Notice: Subject to any disclaimer, the term of this patent is extended or adjusted under 35 U.S.C. 154(b) by 0 days.

(21) Appl. No.: 13/452,587

(22) Filed: Apr. 20, 2012

(65) Prior Publication Data

US 2012/0221051 A1    Aug. 30, 2012

Related U.S. Application Data

(63) Continuation-in-part of application No. 12/960,508, filed on Dec. 5, 2010.

(51) Int. Cl.
*A61B 17/70* (2006.01)

(52) U.S. Cl.
USPC .......................................................... 606/249

(58) Field of Classification Search
CPC ........... A61B 17/7005; A61B 17/7067; A61B 17/7068
USPC .................................... 606/248, 249
See application file for complete search history.

(56) References Cited

U.S. PATENT DOCUMENTS

| | | | |
|---|---|---|---|
| 4,657,550 A | 4/1987 | Daher | |
| 5,290,312 A | 3/1994 | Kojimoto | |
| 5,496,318 A | 3/1996 | Howland | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,312,431 B1 | 11/2001 | Asfora | |
| 6,562,074 B2 | 5/2003 | Gerbec | |
| 6,695,842 B2 | 2/2004 | Zucherman et al. | |
| 7,029,473 B2 | 4/2006 | Zucherman et al. | |
| 7,048,736 B2 | 5/2006 | Robinson | |
| D530,423 S | 10/2006 | Miles | |
| 7,306,628 B2 | 12/2007 | Zucherman et al. | |
| 7,481,839 B2 | 1/2009 | Zucherman et al. | |
| 7,727,233 B2 | 6/2010 | Blackwell et al. | |
| 7,846,186 B2 * | 12/2010 | Taylor | 606/249 |
| 7,857,815 B2 | 12/2010 | Zucherman et al. | |
| 8,292,927 B2 * | 10/2012 | Rouleau et al. | 606/257 |
| 8,419,772 B2 * | 4/2013 | Thompson et al. | 606/254 |
| 2005/0143738 A1 | 6/2005 | Zucherman | |
| 2005/0196420 A1 | 9/2005 | Zucherman et al. | |
| 2005/0203624 A1 | 9/2005 | Serhan | |
| 2006/0085070 A1 | 4/2006 | Kim | |
| 2006/0264938 A1 | 11/2006 | Zucherman et al. | |
| 2007/0010813 A1 | 1/2007 | Zucherman et al. | |

(Continued)

FOREIGN PATENT DOCUMENTS

| EP | 1138268 | 10/2001 |
|---|---|---|
| EP | 2275047 A2 | 1/2011 |

(Continued)

*Primary Examiner* — Ellen C Hammond
(74) *Attorney, Agent, or Firm* — FisherBroyles, LLP; Anthony J. DoVale

(57) ABSTRACT

An implantable device and method for fixation of spinous processes is presented. The device has first and second spaced plates configured for attachment to portions of adjacent spinous processes. The device can also have an implant configured for insertion between two adjacent spinous processes, but need not necessarily. The method has the steps of assembling the components of the implantable device and otherwise inserting them into position onto, between, and/or adjacent two desired spinous processes.

14 Claims, 20 Drawing Sheets

(56) References Cited

U.S. PATENT DOCUMENTS

| | | |
|---|---|---|
| 2007/0093830 A1 | 4/2007 | Zucherman et al. |
| 2007/0219634 A1 | 9/2007 | Greenhalgh |
| 2007/0270827 A1 | 11/2007 | Lim |
| 2007/0276381 A1 | 11/2007 | Butler |
| 2008/0177271 A1 | 7/2008 | Yeh |
| 2008/0183211 A1 | 7/2008 | Lamborne et al. |
| 2009/0254123 A1* | 10/2009 | Pafford et al. ............... 606/254 |
| 2011/0077687 A1* | 3/2011 | Thompson et al. ........... 606/254 |
| 2011/0160772 A1 | 6/2011 | Arcenio |
| 2012/0016418 A1* | 1/2012 | Chin et al. .................... 606/249 |
| 2012/0101528 A1 | 4/2012 | Souza et al. |
| 2012/0109203 A1* | 5/2012 | Dryer et al. ................... 606/249 |

FOREIGN PATENT DOCUMENTS

| | | |
|---|---|---|
| MX | 2009005457 | 2/2009 |
| WO | 2011094062 A1 | 8/2011 |
| WO | 2012012771 A1 | 1/2012 |

* cited by examiner

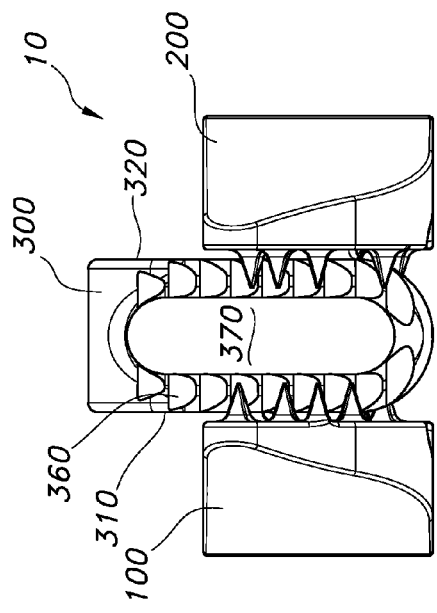
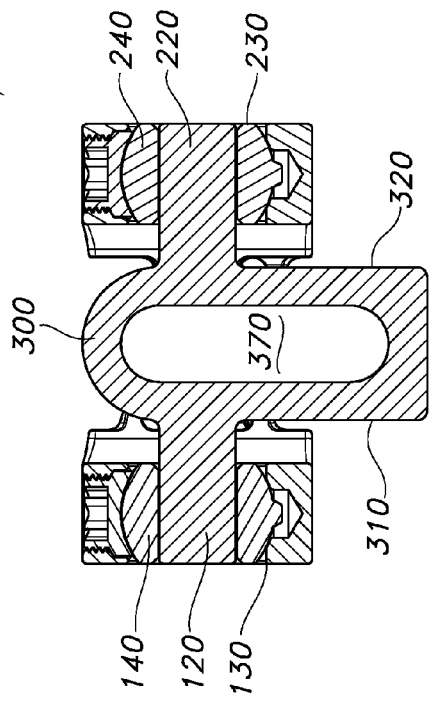
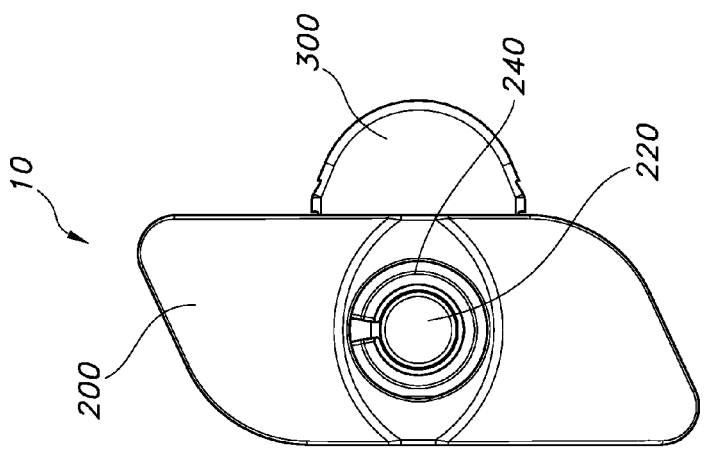
FIG. 5
FIG. 6
FIG. 4

US 8,603,143 B2

SPINOUS PROCESS FIXATION APPARATUS

CONTINUITY

This application claims the benefit of and is a continuation-in-part of U.S. patent application Ser. No. 12/960,508 entitled "Spinous Process Fixation Apparatus and Method" filed on Dec. 5, 2010, which is incorporated herein in its entirety by reference.

FIELD OF THE INVENTION

This invention relates generally to spinal surgery, and more particularly to devices for stabilization of the spine in association with placement of an interbody construct for interbody fusion or the like.

BACKGROUND OF THE INVENTION

Varieties of interbody fusion devices are widely used following partial or total discectomies for stabilization of the spine at the site. Some stabilization devices are anchored to the pedicles. With several systems, the use of the pedicles requires screws or other anchoring devices that occupy significant space and involve muscle dissection and associated work-time for implantation. Nerve root injuries are a well-known potential complication of placement of screws in the pedicles.

The interspinous process devices are designed to increase the interspinous process height, thereby increasing the sagittal cross-sectional area of the foramen, where the nerve roots pass away out of the spine. It is thought that these devices may also unload the facet joints, and perhaps the intervertebral disc. They may limit spinal extension. This backward bending position may be painful for patients with spinal stenosis because it reduces the space available for the nerve roots in the exiting foraminal openings.

In addition to interspinous process implants, interspinous process fixation devices are also common to fix adjacent spinous processes to each other to stabilize the spinal motion-segment as an adjunct to spinal fusion. Current systems include spinous process plates that are fixed with adjacent spinous processes sandwiched therebetween.

SUMMARY

Presented herein is an implantable device for fixation of spinous processes. The device comprises first and second spaced plates configured for attachment to portions of adjacent spinous processes. In one aspect, each plate has a first and second surface, whereby the first surface of the first plate is configured to face the second surface of the second plate.

In another aspect, the device comprises an implant with a first face, an opposed second face, a top portion, and a bottom portion. The implant is configured for insertion between two adjacent spinous processes. In one aspect, the implant is an interbody cage. When positioned, the first face of the implant faces the first surface of the first plate and the second face of the implant faces the second surface of the second plate. In this aspect, the first plate is connected to a portion of the implant substantially adjacent the first face, and the second plate is connected to a portion of the implant substantially adjacent the second face. It is understood that implants of varying size and shape are disclosed herein, as well as alternate embodiments with no implant.

In addition to the implantable device described herein, presented herein is a method of fixation of spinous processes of a subject. In one aspect, the method comprises assembling the components of the implantable device (i.e. the first and second plates, and the implant), exposing at least one desired spinous process, inserting the implant between two adjacent spinous processes, joining the first and second plates to the implant with a portion of the spinous processes being therebetween, compressing the plates onto the first and second spinous processes, and maintaining the compression of the plates while affixing the plates with respect to the implant.

Related methods of operation are also provided. Other apparatuses, methods, systems, features, and advantages of the interspinous process device and the method of its use will be or become apparent to one with skill in the art upon examination of the following figures and detailed description. It is intended that all such additional apparatuses, methods, systems, features, and advantages be included within this description, be within the scope of the interspinous process device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 4 is right side view of the implantable device of FIG. 2;

FIG. 5 is a plan view of the implantable device of FIG. 2;

FIG. 6 is cross-sectional bottom elevational view of the implantable device of FIG. 2, cut along line 6-6 in FIG. 3;

DESCRIPTION OF THE INVENTION

Figure 1:
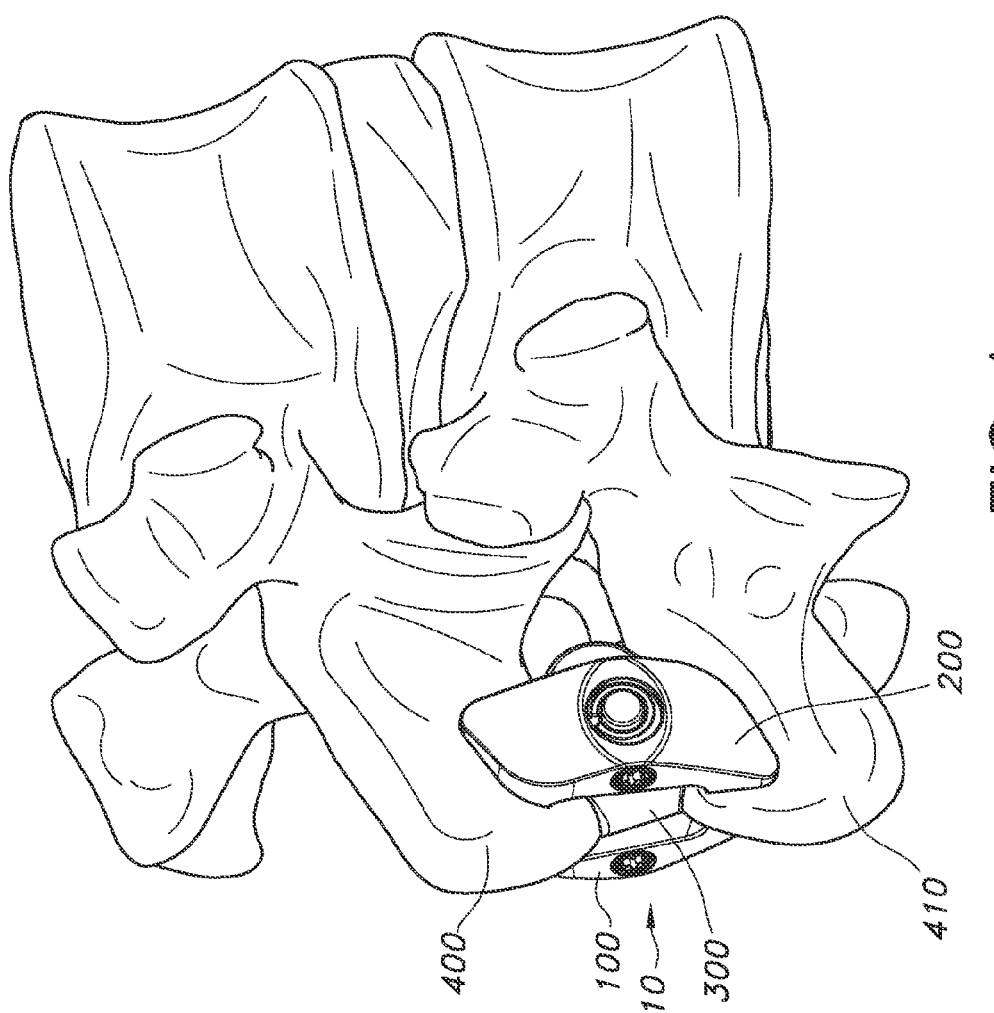
FIG. 1 is a perspective view of one aspect of an implantable device for the fixation of spinous processes, shown in-situ between first and second spinous processes.
Figure 3:
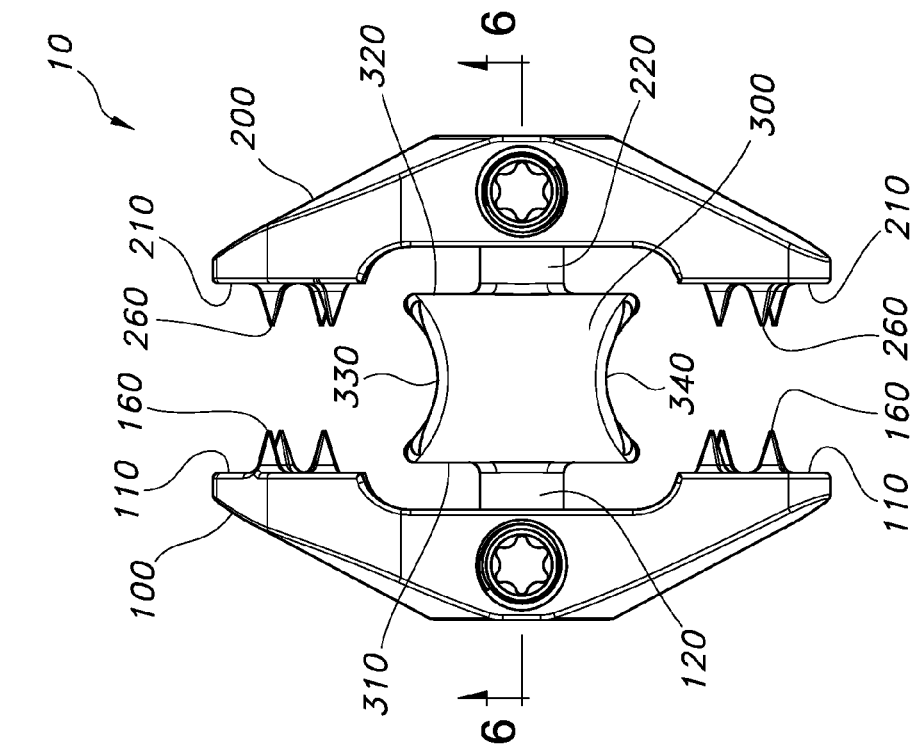
FIG. 3 is a rear elevational view of the implantable device of FIG. 2.
Figure 2:
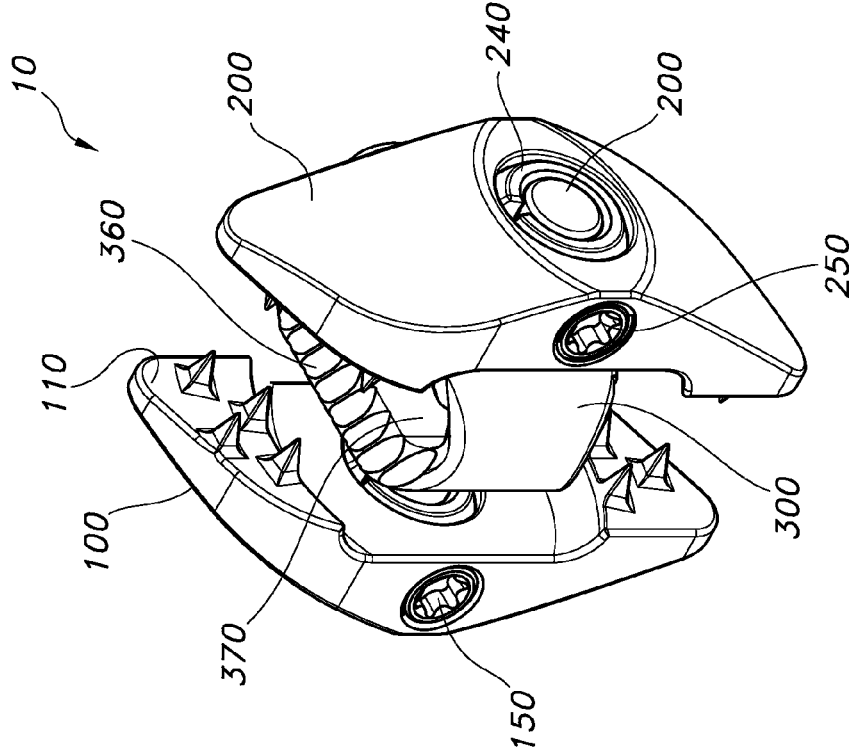
FIG. 2 is a perspective view of one aspect of the implantable device of FIG. 1.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

In one aspect, presented herein is an implantable device 10 for fixation of spinous processes. The device comprises first and second spaced plates 100, 200 configured for attachment to portions of adjacent spinous processes. In one aspect, each plate has a first and second surface, whereby the first surface 110 of the first plate 100 is configured to face the second surface 210 of the second plate 200.

In another aspect, the device comprises an implant 300 with a first face 310, an opposed second face 320, a top portion 330, and a bottom portion 340. The implant 300 is configured for insertion between two adjacent spinous processes. In one aspect, the implant is an interbody cage. When positioned, the first face 310 of the implant faces the first surface 110 of the first plate 100 and the second face 320 of the implant faces the second surface of the second plate 200. In this aspect, the first plate is connected to a portion of the implant substantially adjacent the first face, and the second plate is connected to a portion of the implant 300 substantially adjacent the second face.

It is beneficial for the plates to be able to move with respect to the implant in order to adjust to the contour of the portions of the spinous processes onto which they attach. In one aspect, the plates can move polyaxially with respect to the implant. In another aspect, one or both of the first and second plates are pivotally connected to the respective portions of the implant. As such, there exist several options to accomplish this feature.

Figure 7:
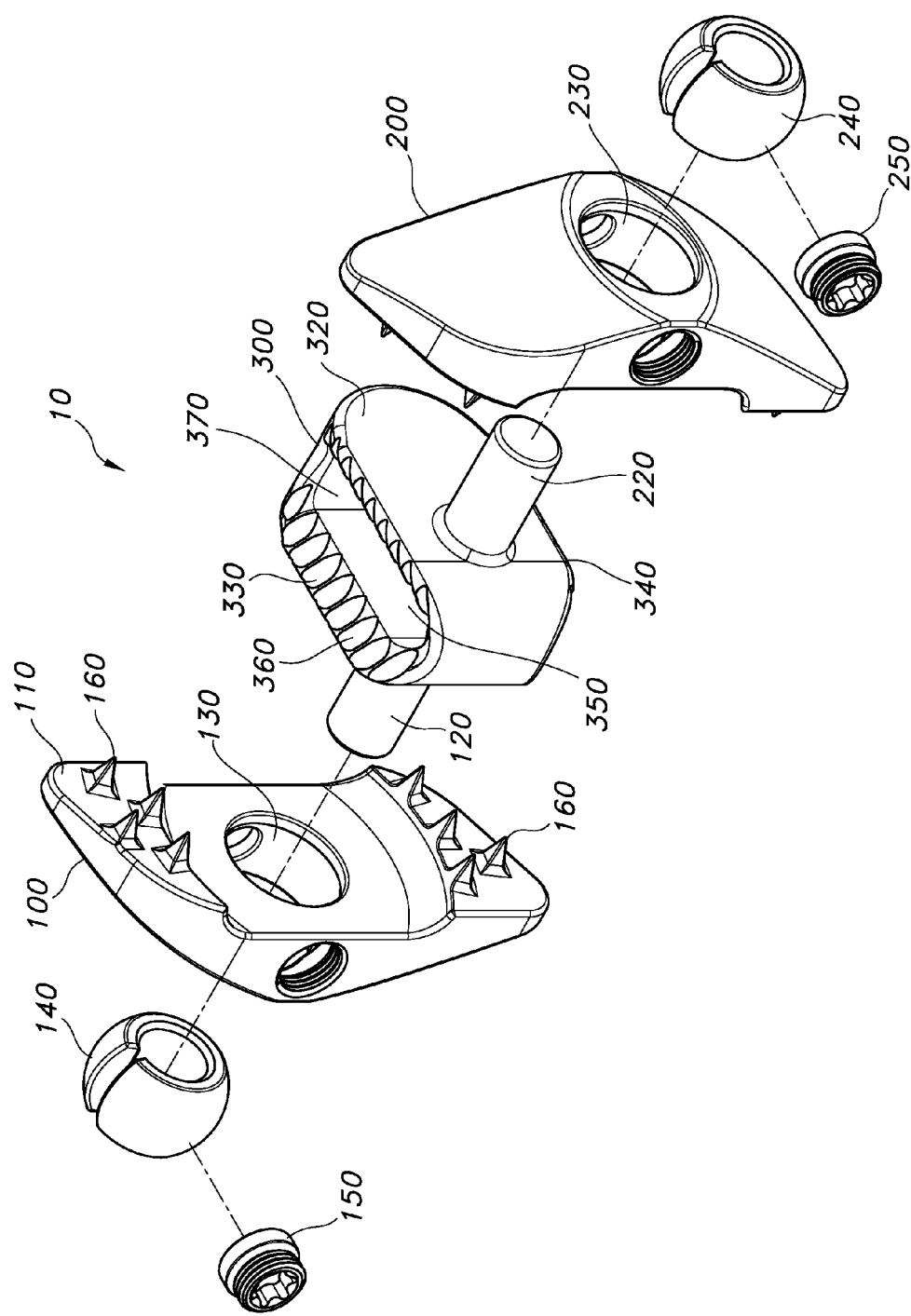
FIG. 7 is an exploded perspective view of the implantable device of FIG. 2.
Figure 9:
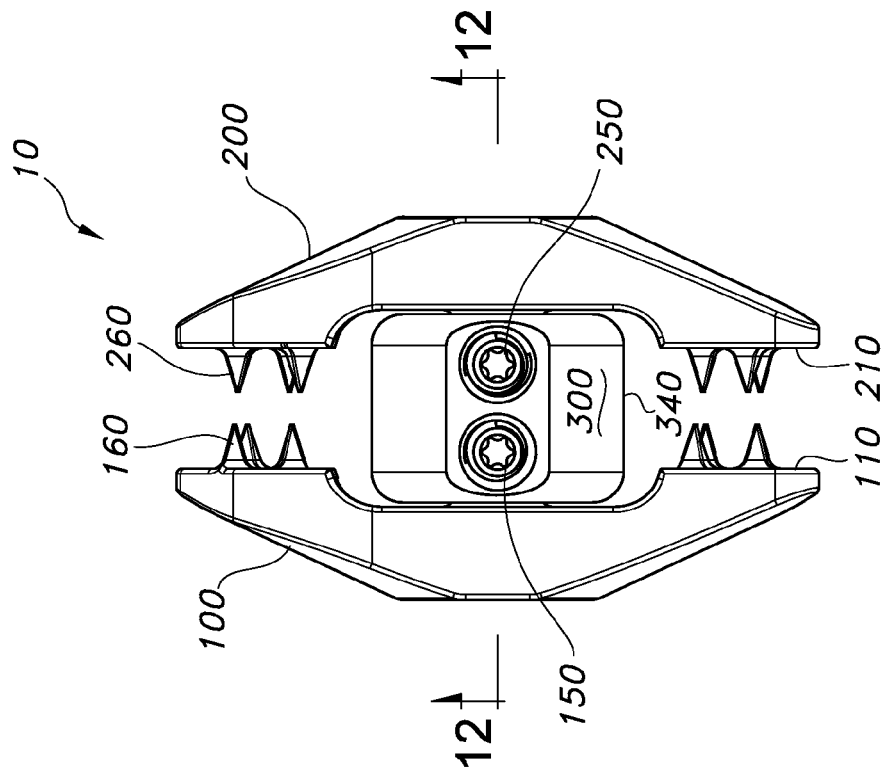
FIG. 9 is a rear elevational view of the implantable device of FIG. 8.
Figure 8:
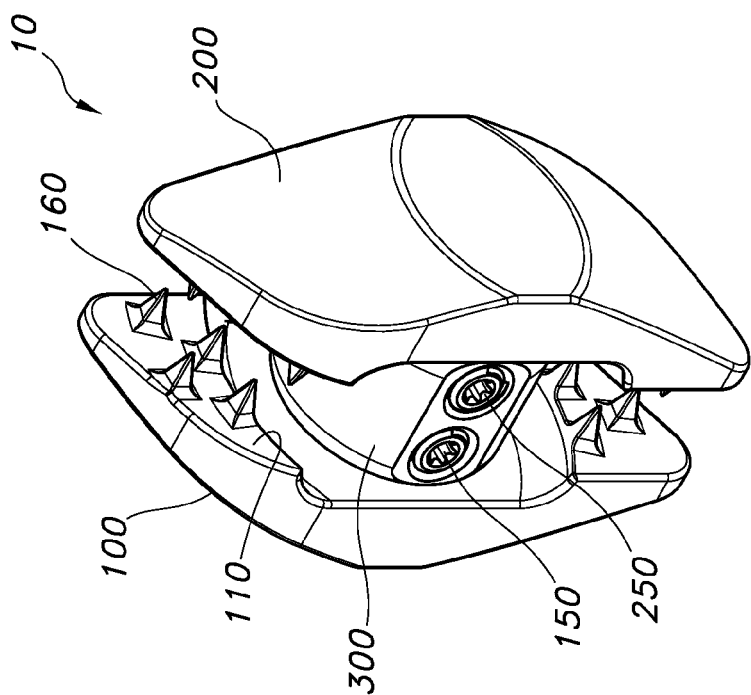
FIG. 8 is a perspective view of one aspect of the implantable device for the fixation of spinous processes.
Figure 11:
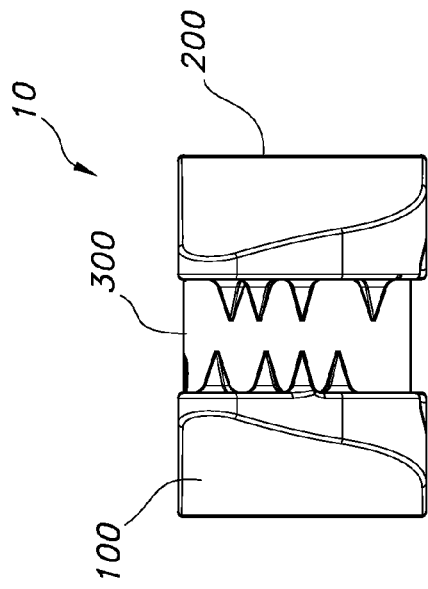
FIG. 11 is a plan view of the implantable device of FIG. 8.
Figure 12:
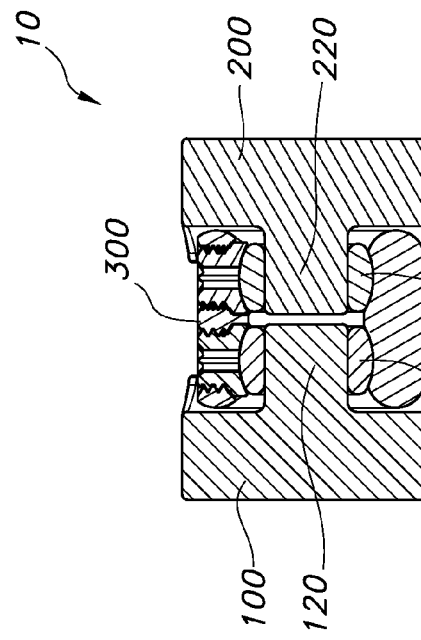
FIG. 12 is cross-sectional bottom elevational view of the implantable device of FIG. 8, cut along line 12-12 in FIG. 9.
Figure 10:
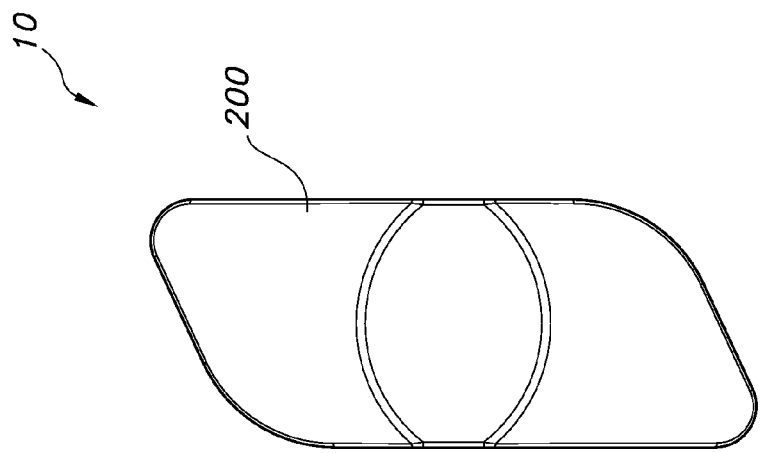
FIG. 10 is right side view of the implantable device of FIG. 8.

In one aspect, the implant comprises a first post 120 projecting therefrom the first face and a second post 220 projecting therefrom the second face. As illustrated in FIG. 7, in one aspect, the first and second posts are substantially normal to the respective first and second faces. However, it is contemplated that the first and second post can be positioned at an acute angle relative to the respective first and second faces of the implant 300.

In another aspect, the first plate comprises a first socket 130 for complimentary receipt of the first post 120 and the second plate 200 comprises a second socket 230 for complimentary receipt of the second post 220. In this aspect, a first internal collar 140 can be positioned within the first socket 130 and a second internal collar 240 can be positioned within the second socket 230. The collars, thus, can be configured to engage a portion of the respective first and second posts. In yet another aspect, each internal collar can be configured to pivot within each respective socket, thereby permitting polyaxial movement of the first and second plates with respect to the implant. The collars can have an external diameter that is larger than the diameter of the socket, thereby resisting movement of the collars into or out of the socket. Additionally, the collars may comprise a slit, which can be compressed for insertion into each socket during manufacturing.

In one exemplified aspect, there can be set screws 150, 250 configured to interface with each collar to tighten the collars thereto the respective first and second posts. The collars are configured to interface at a desired connection point along the particular post with which it interfaces, thereby selectively controlling the distance between the first and second surface of the first and second plates, respectively.

In another aspect, in lieu of, or in addition to, the polyaxial movement permitted by the collar and socket combination, the posts may comprise flexible material, thereby permitting polyaxial movement of the first and second plates with respect to the implant. As such, the plates can be connected thereto the posts without the use of collars, as shown in FIGS. 14-19.

Figure 13:
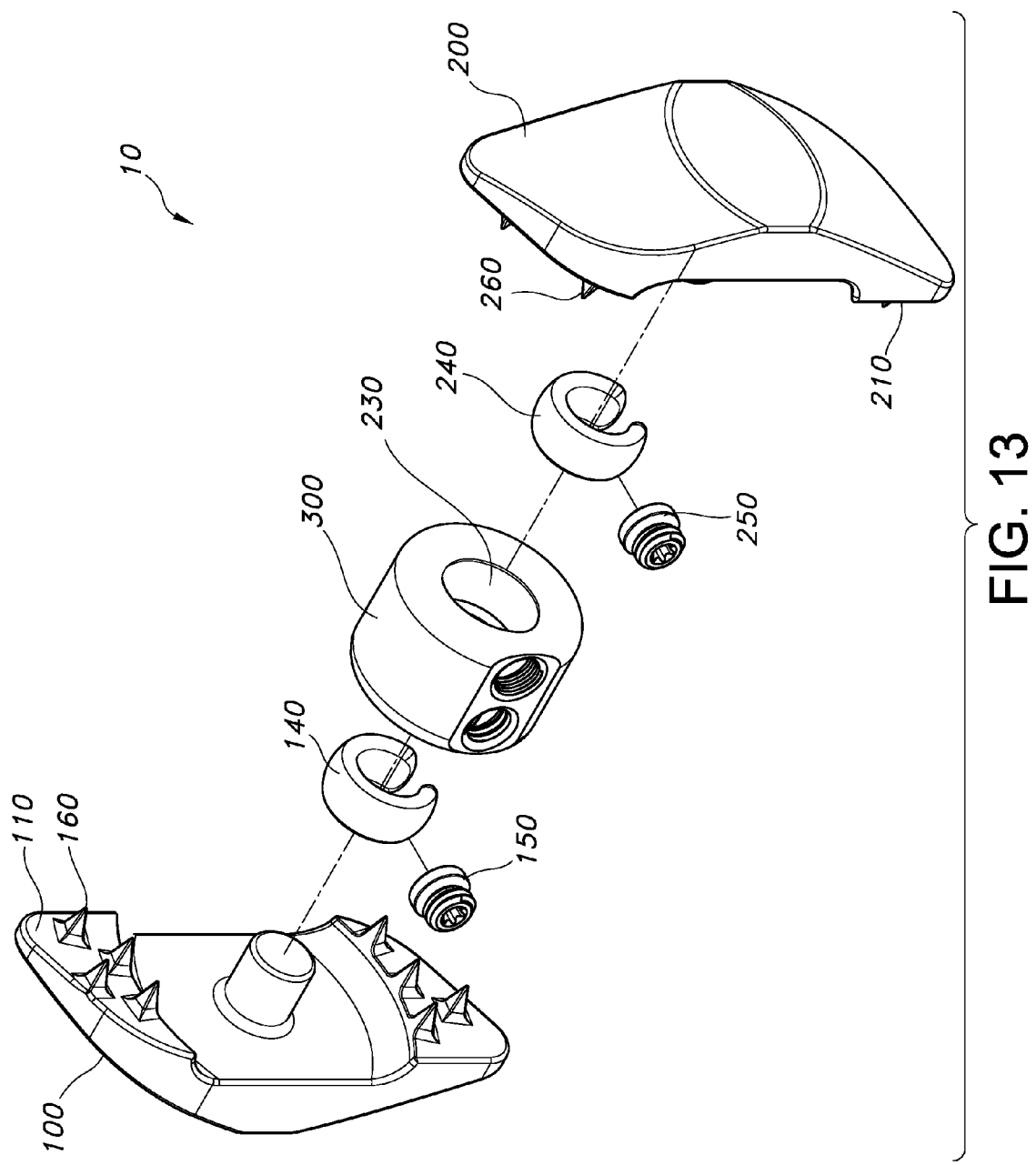
FIG. 13 is an exploded perspective view of the implantable device of FIG. 8.
Figures 14, 15:
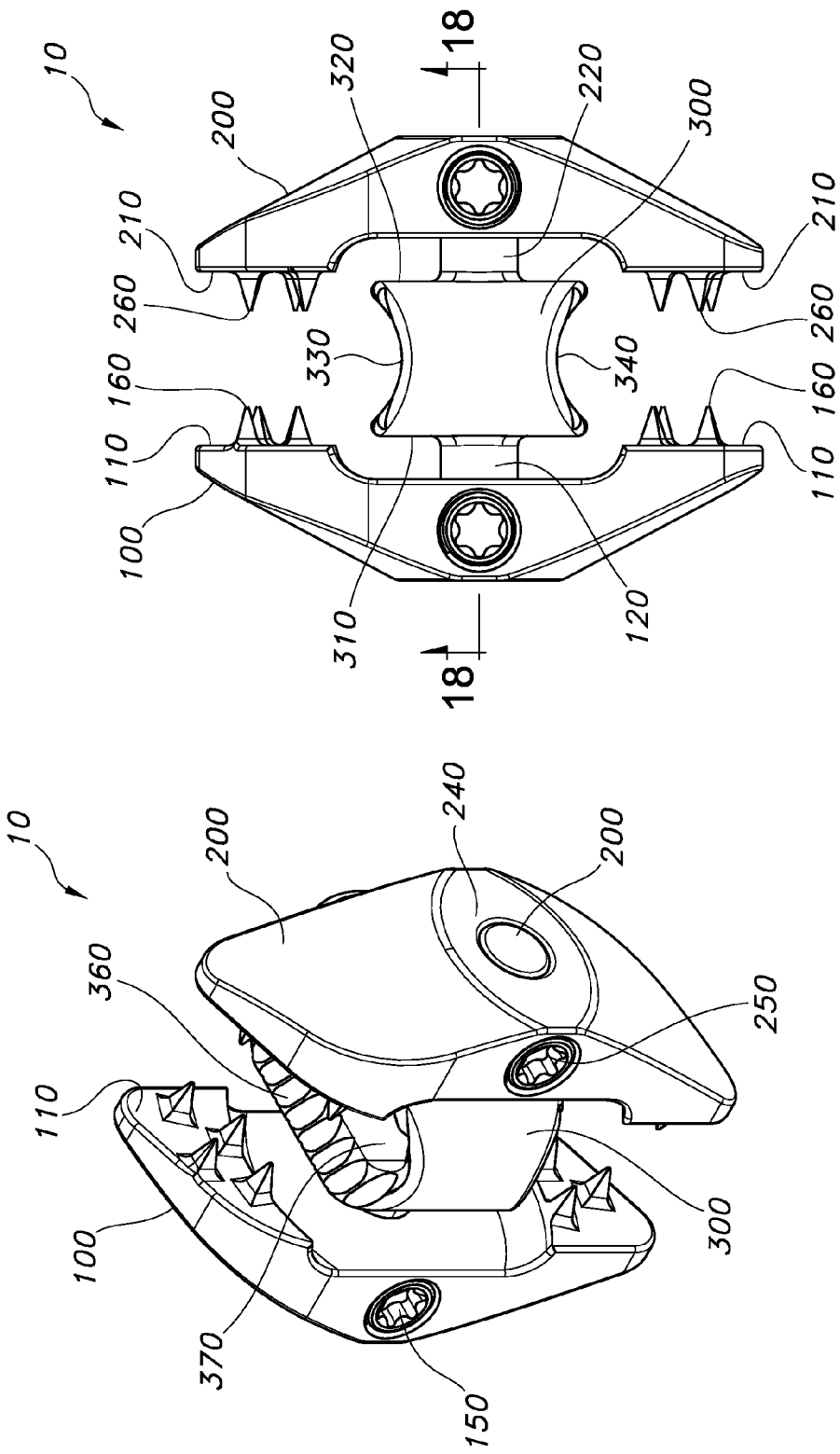
FIG. 14 is a perspective view of one aspect of the implantable device for the fixation of spinous processes showing one aspect with at least one substantially flexible post.
FIG. 15 is a rear elevational view of the implantable device of FIG. 14.
Figure 17:
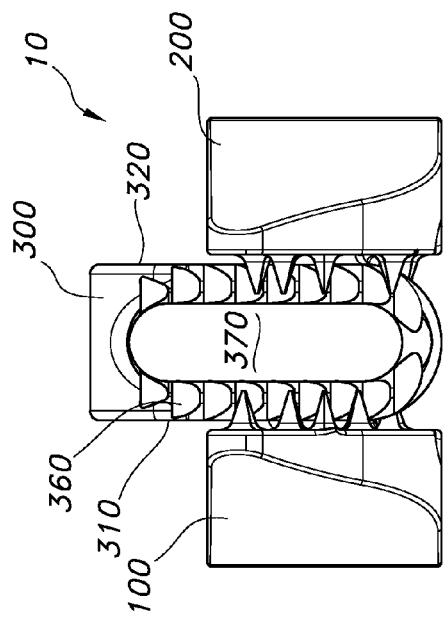
FIG. 17 is a plan view of the implantable device of FIG. 14.
Figure 18:
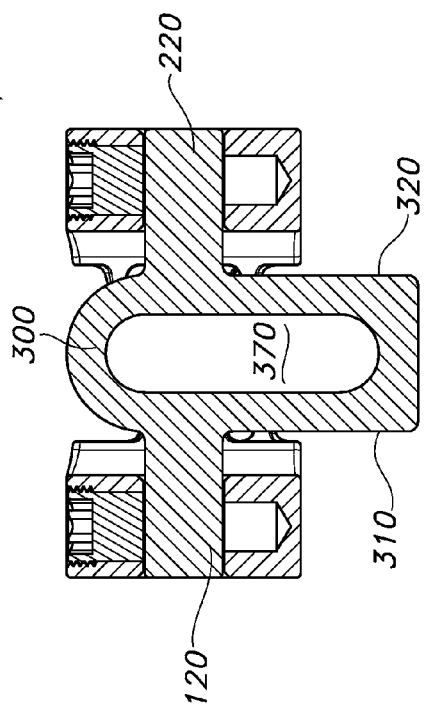
FIG. 18 is cross-sectional bottom elevational view of the implantable device of FIG. 14, cut along line 18-18 in FIG. 15.
Figure 16:
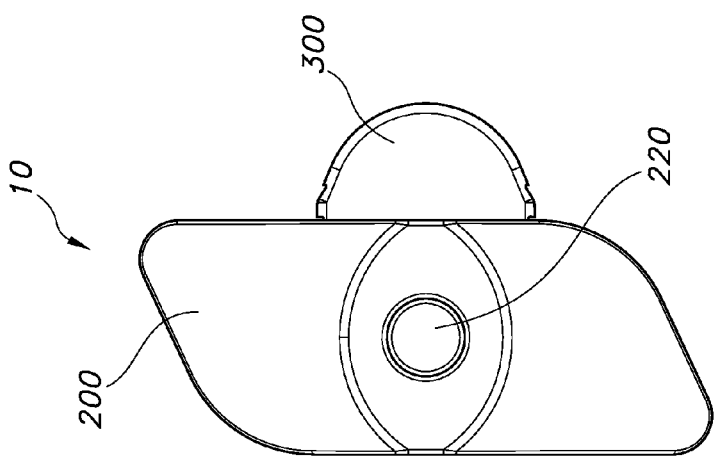
FIG. 16 is right side view of the implantable device of FIG. 14.
Figure 19:
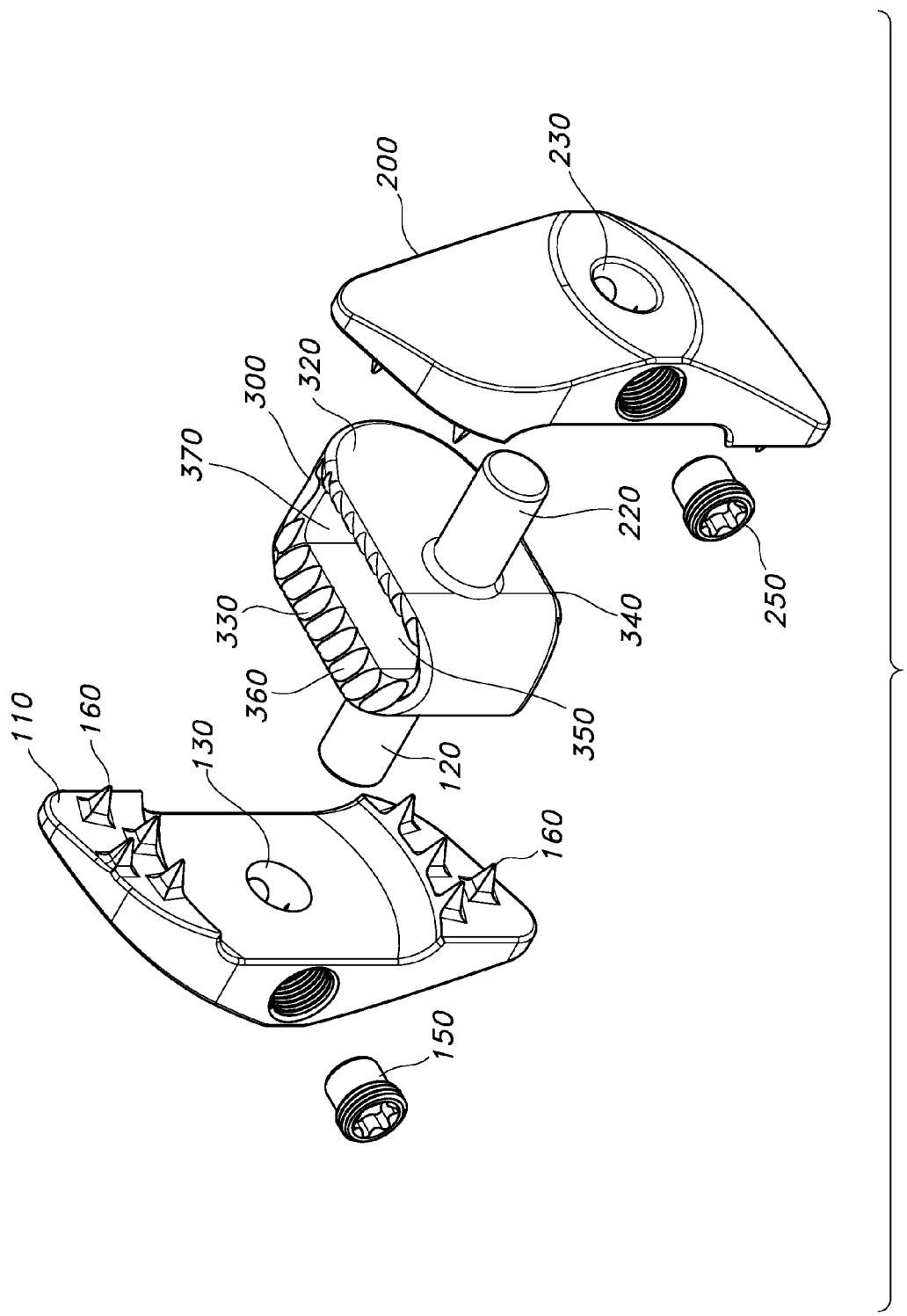
FIG. 19 is an exploded perspective view of the implantable device of FIG. 14.
Figure 20:
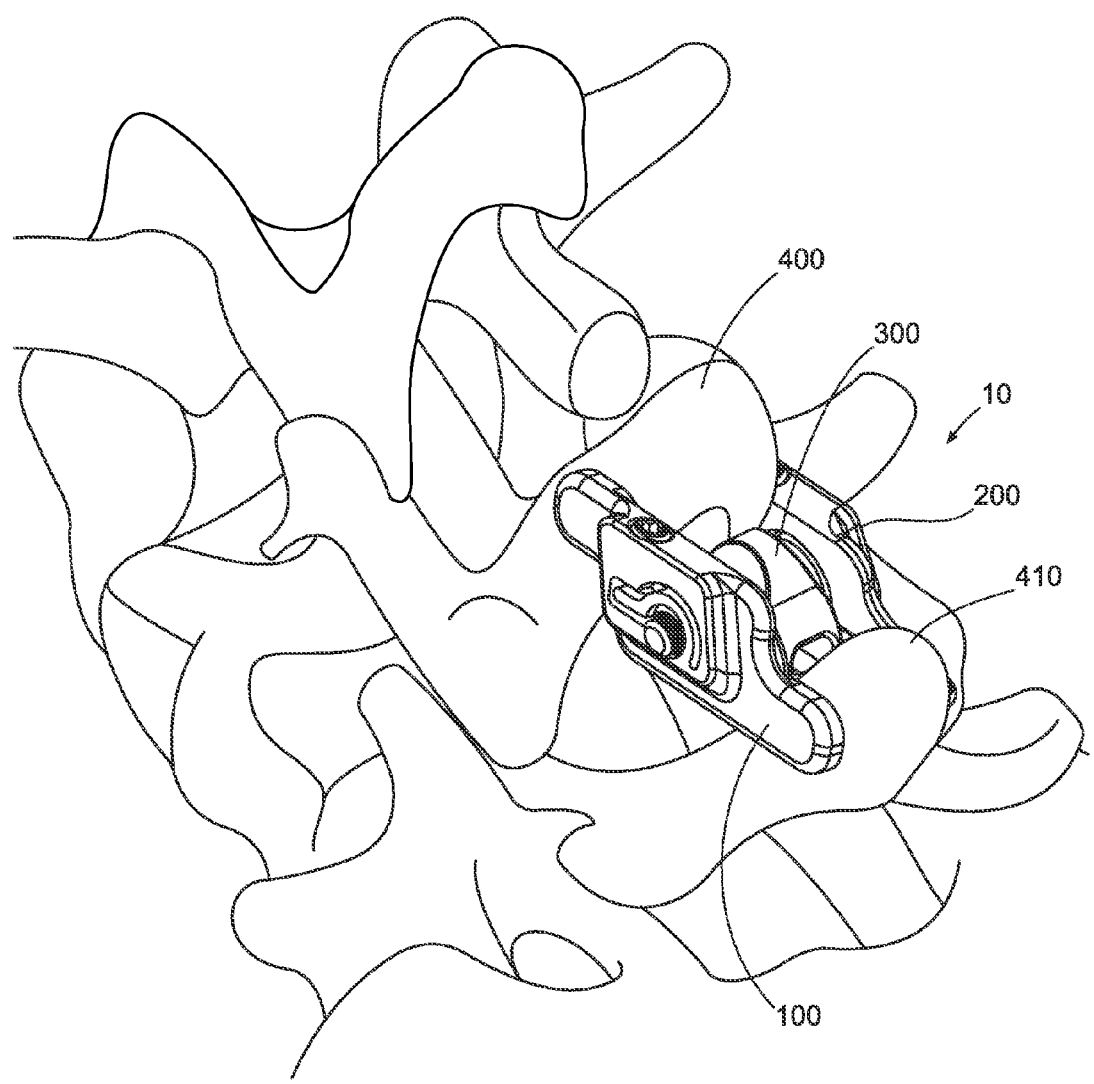
FIG. 20 is a perspective view of one aspect of an implantable device for the fixation of spinous processes, shown in-situ between first and second spinous processes.
Figure 21:
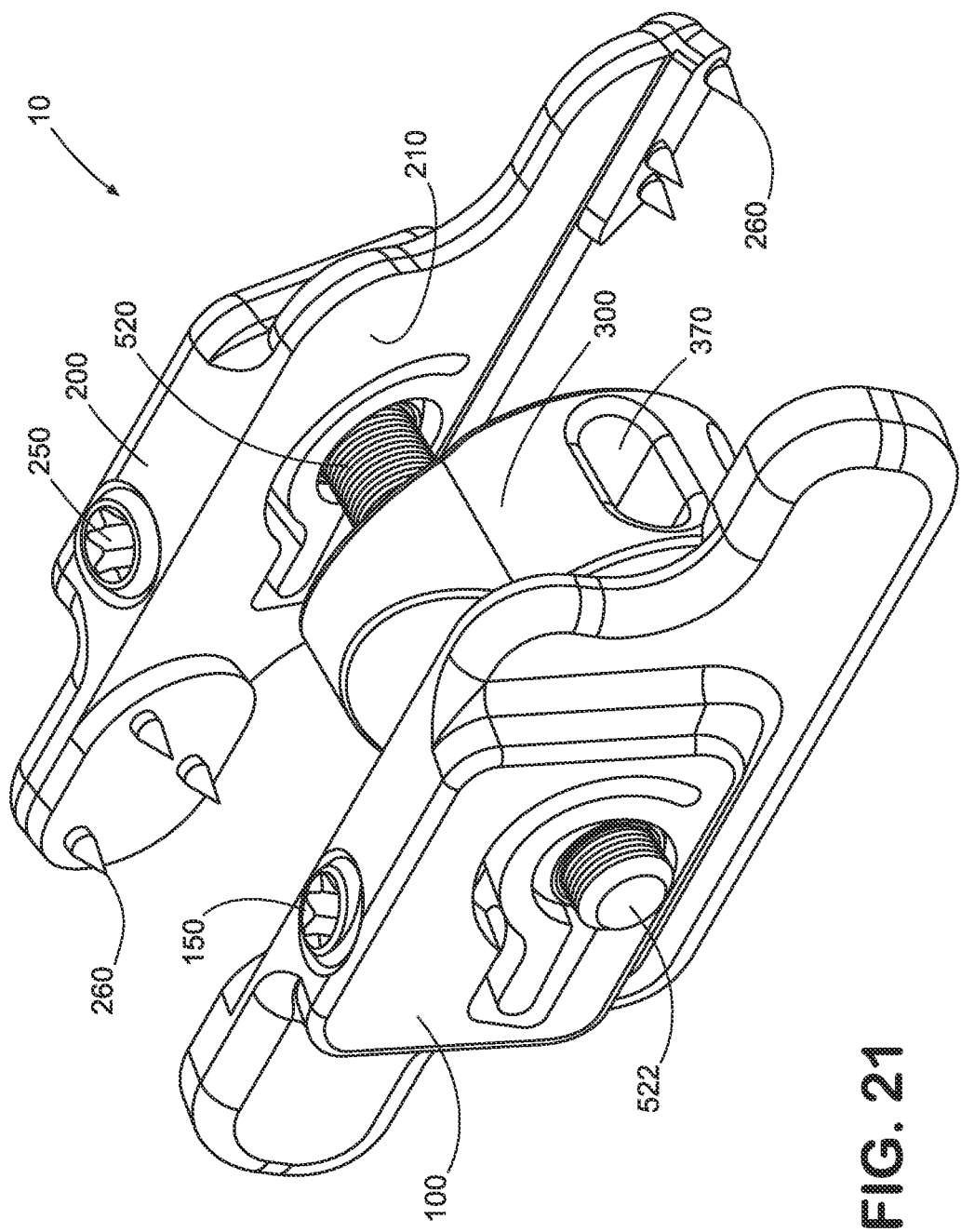
FIG. 21 is a perspective view of one aspect of the implantable device of FIG. 20.
Figure 22:
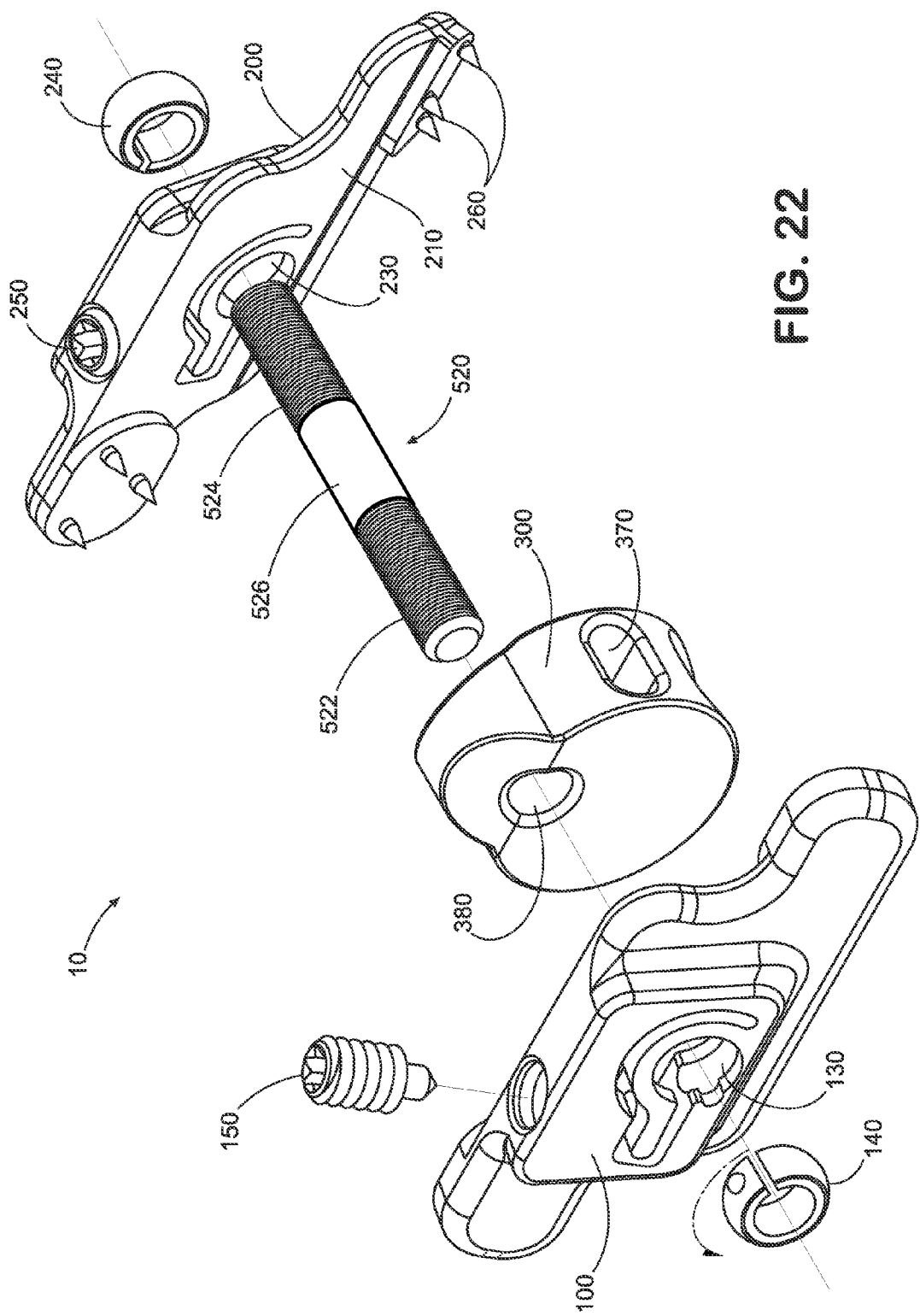
FIG. 22 is an exploded perspective view of the implantable device of FIG. 20.
Figure 23A:
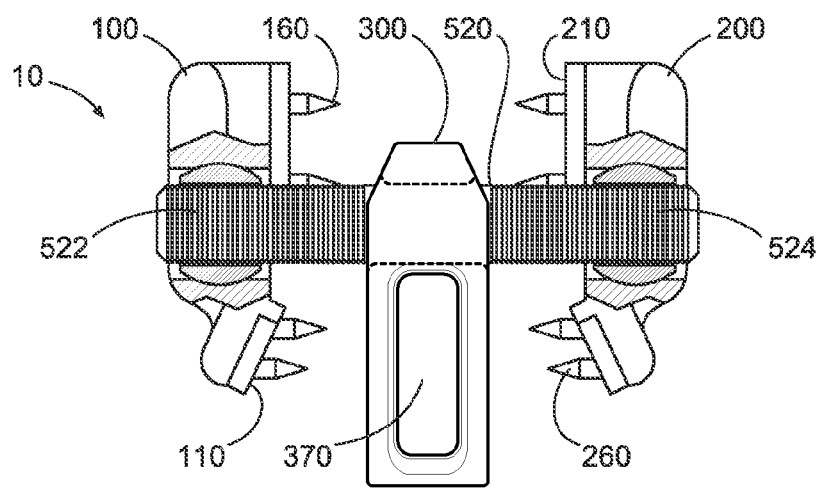
FIGS. 23A-23C are cross-sectional bottom elevational views of the implantable device of FIG. 20, showing the first plate and the second plates at various angles with respect to one another.
Figure 23B:
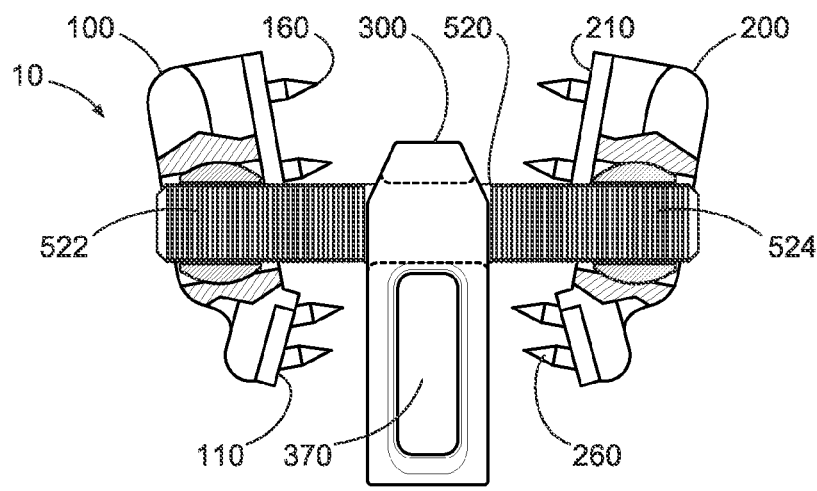
Figure 23C:
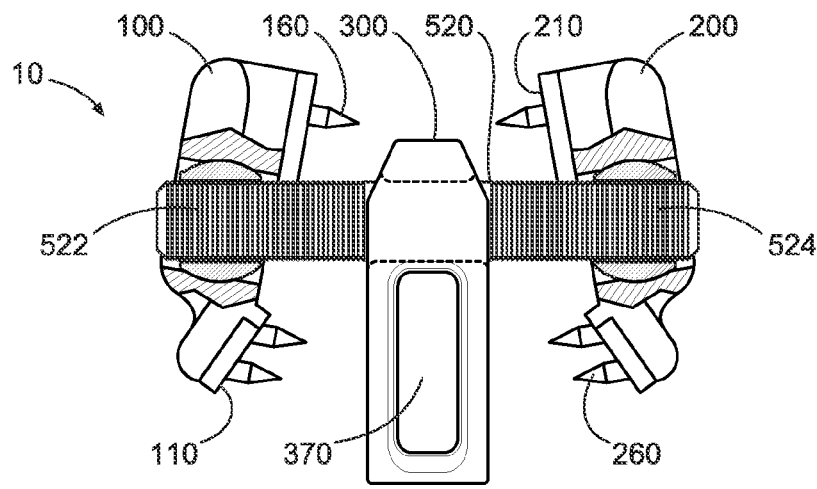
Figure 24A:
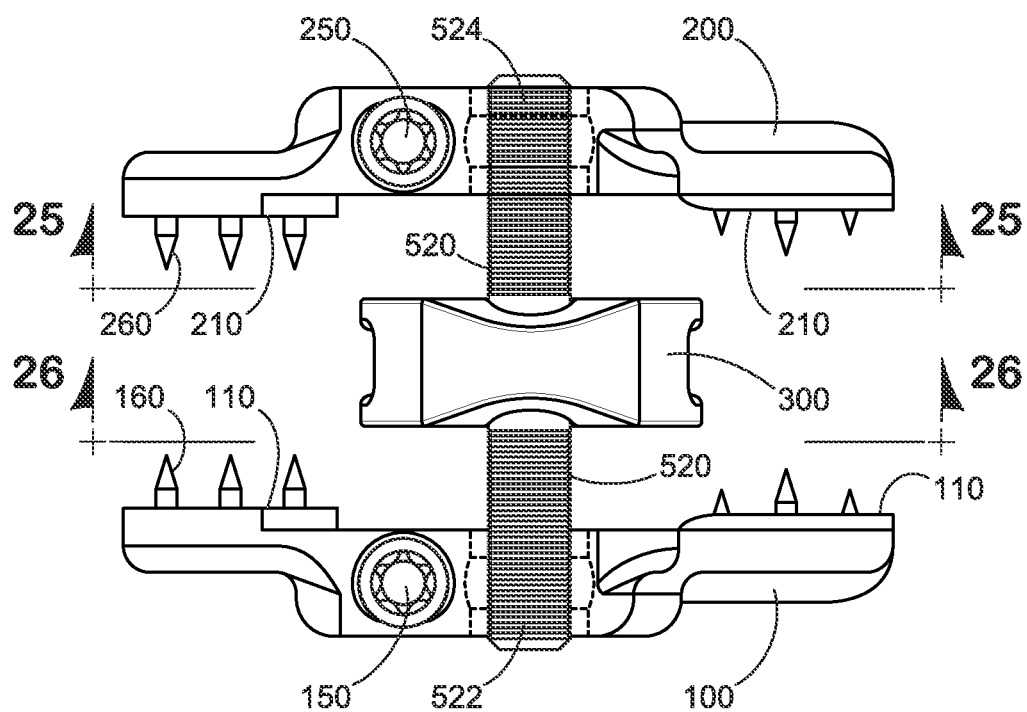
FIGS. 24A and 24B are partially transparent top plan views of the implantable device of FIG. 20, showing the two plates having the ability to be connected at various connection points on the post and having the ability for polyaxial movement with respect thereto.
Figure 24B:
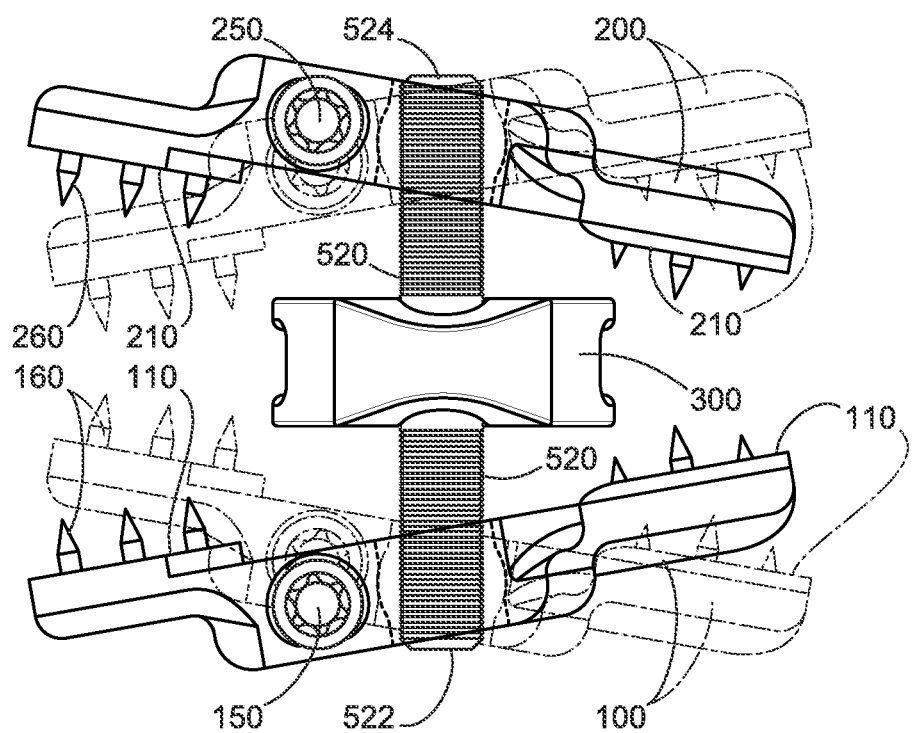
Figure 25:
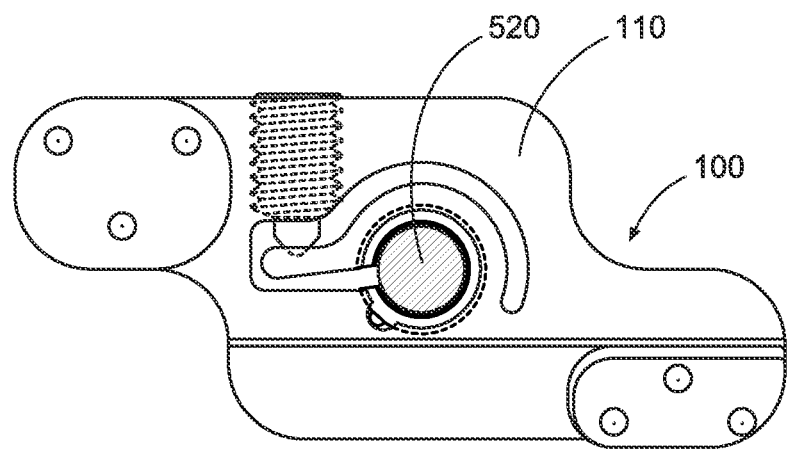
FIG. 25 is left side elevational view of one aspect of a first plate of the implantable device of FIG. 20.
Figure 26:
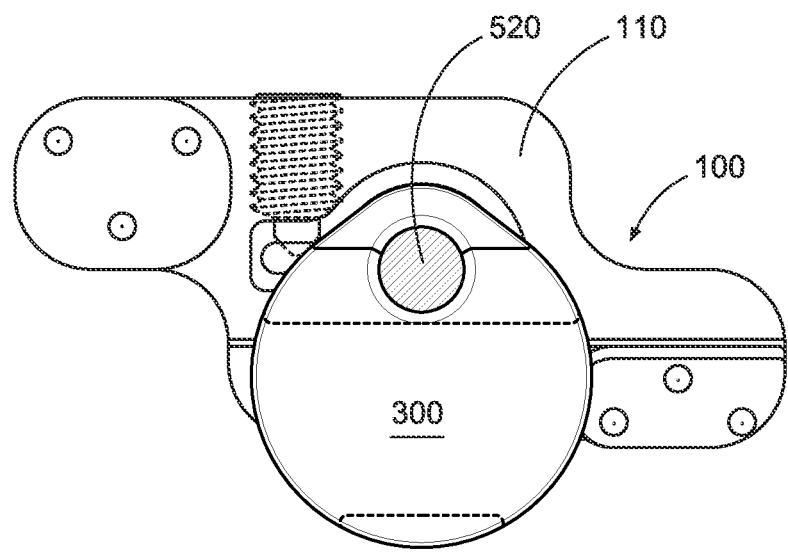
FIG. 26 is a right side elevational view of one aspect of a first plate of the implantable device of FIG. 20, showing an implant positioned there between the first and second spaced plates.
Figure 27:
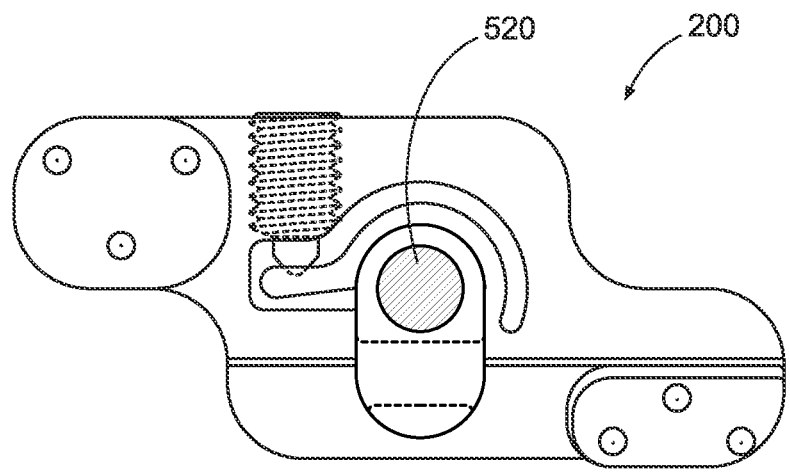
FIG. 27 is a right side elevational view of one aspect of a second plate of the implantable device of FIG. 20.
Figure 28:
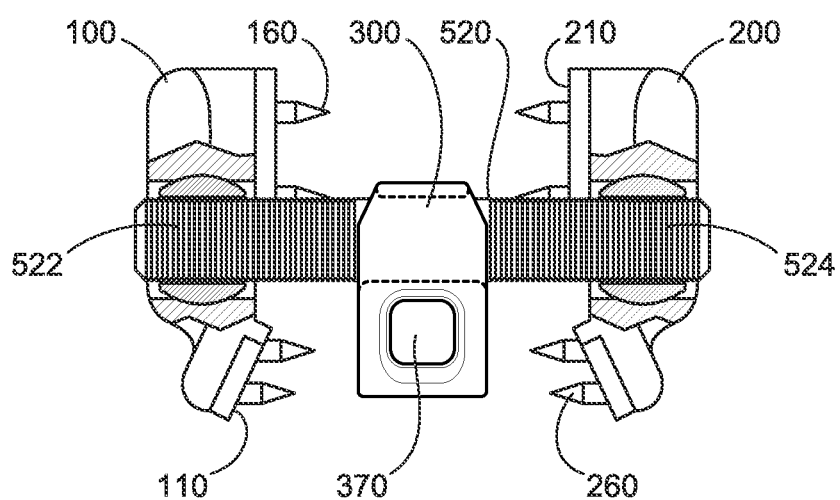
FIG. 28 is a front cross-sectional elevational view of the implantable device of FIG. 20.
Figure 29:
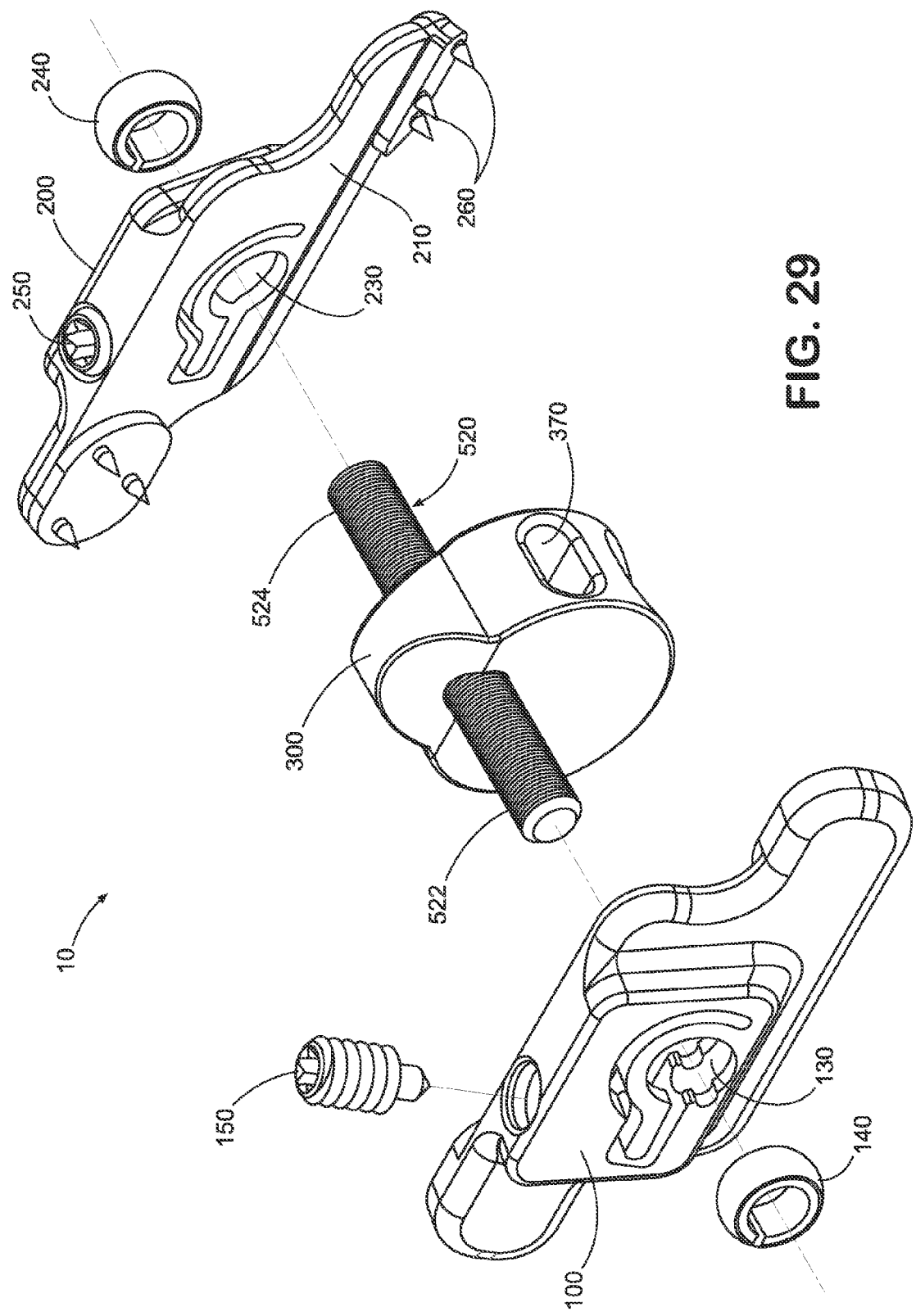
FIG. 29 an exploded perspective view of the implantable device of FIG. 20, showing the post positioned therethrough an implant.
Figure 30:
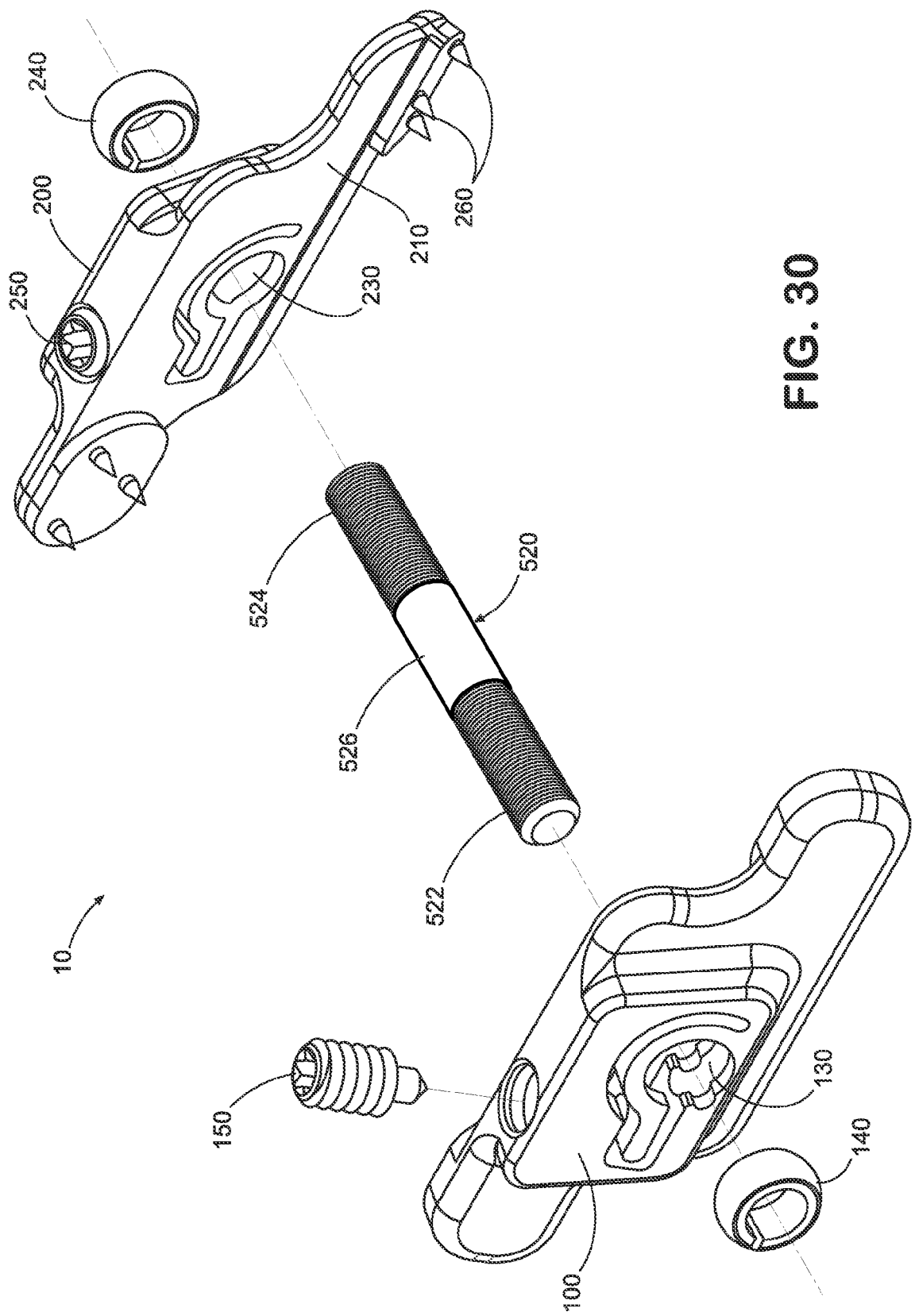
FIG. 30 is an exploded perspective view of the implantable device of FIG. 20, showing the device without an implant.
Figure 31:
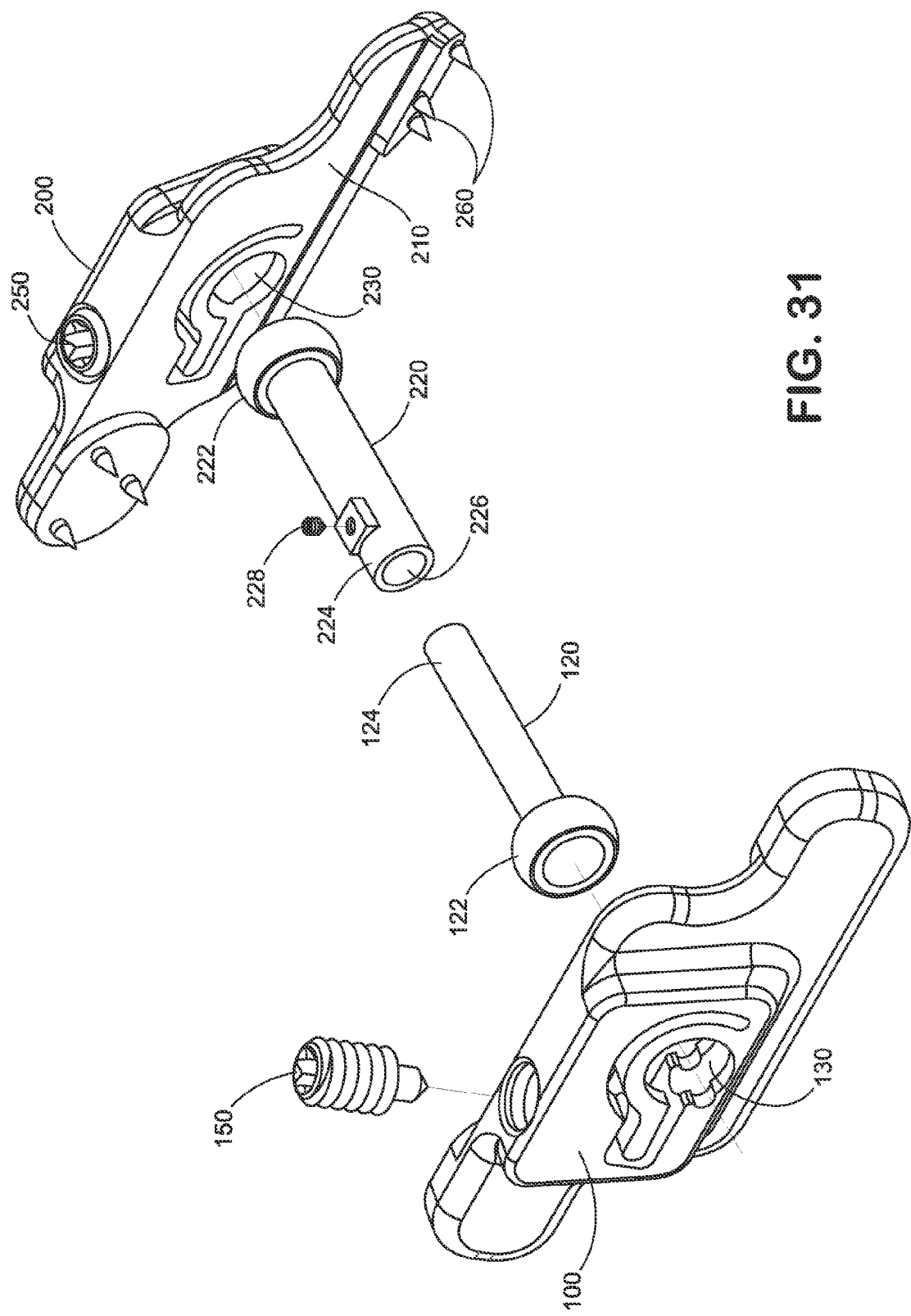
FIG. 31 is an exploded perspective view of one aspect of an implantable device for the fixation of spinous processes, showing an embodiment wherein a first post is configured to be telescopingly received by an interior longitudinal cavity of a second post.

In another exemplified aspect, as shown in FIG. 13, the posts can project therefrom the first and second surfaces of the first and second plates, respectively, rather than from the first and second faces 310, 320 of the implant. As such, in one aspect, the first and second posts are substantially normal to the respective first and second surfaces. In this aspect, the implant comprises a first socket for complimentary receipt of the first post and a second socket 230 for complimentary receipt of the second post.

Similar to the aspect described above, in another aspect, a first internal collar 140 is positioned within the first socket 130 and a second internal collar 240 is positioned within the second socket. The first and second collars are configured to engage a portion of the respective first and second posts 120, 220. In one aspect, they can engage the posts along the length of the post, thereby allowing for variance in the distance between the two plates.

In one exemplified aspect, each internal collar can pivot within each respective socket, thereby permitting polyaxial movement of the first and second plates with respect to the implant 300. Additionally, as mentioned herein, in another aspect, the first post and the second post are flexible, thereby permitting polyaxial movement of the first and second plates with respect to the implant.

At least one of the first and second surfaces 110, 210 of the plates 100, 200, in one aspect, comprises teeth 160, 260 for frictional engagement of spinous processes. As can be appreciated, both the first and second surfaces can comprise teeth. The teeth 160, 260, for example, engage the spinous processes when the plates are clamped thereon.

In another exemplified aspect, the top portion 330 of the implant defines a longitudinal trough 350 configured for complimentary receipt of a portion of a first spinous process 400. As can be appreciated by one skilled in the relevant art, the bottom portion 340 of the implant may likewise define a longitudinal trough 350 configured for complimentary receipt of a second spinous process 410, which would be adjacent the first spinous process 400.

The longitudinal trough of the top portion can also comprise external edges that have a plurality of consecutive ridges 360 configured for frictional engagement with a portion of the first spinous process. As can be appreciated, the longitudinal trough of the bottom portion may also have external edges with pluralities of consecutive ridges 360 for frictional engagement with a portion of the second spinous process 410. For ease of insertion, the implant can also comprise a tapered distal nose, as illustrated in FIG. 7.

As can be appreciated by one skilled in the art, at times, it can be beneficial to have, in addition to the mechanical fixation, a fusion or other bonding component of the implantable device explained herein. In one exemplified aspect, the implant 300 defines an internal cavity 370 in communication with at least one of the top portion and the bottom portion. In another aspect, the internal cavity 370 is in communication with both the top portion and the bottom portion. In use, the professional may introduce bone cement or bone graft material into the internal cavity to assist in fusion or bonding of the implant with the surrounding spinous processes.

In addition to the implantable device described herein, presented herein is a method of fixation of spinous processes of a subject. The method comprises assembling the components of the implantable device into an implant assembly (i.e. the first and second plates, and the implant), exposing at least one desired spinous process, inserting the implant 300 between two adjacent spinous processes, joining the first and second plates to the implant with a portion of the spinous processes being positioned therebetween, compressing the plates onto the first and second spinous processes, and maintaining the compression of the plates while affixing the plates with respect to the implant.

As mentioned herein, the implant can comprise a first and second post extended therefrom the first and second faces of the implant 300, each post configured for engagement with the first and second plates. In this aspect, the step of joining the first and second plates with the implant can comprise sliding the first plate 100 onto the first post 120 and the second plate 200 onto the second post whereby portions of the first and second spinous processes are positioned in a space between the first and second surfaces and affixing the first plate to the first post and the second plate to the second post. Where the first and second plates comprise collars with set screws, affixing the first and second plates onto the first and second posts can comprise merely tightening the set screws.

In one aspect of the method, the method comprises the step of angulating one or both of the first and second plates relative to each other in at least one plane during compression on the spinous process. In another aspect, the method comprises angulating the two plates in two planes during compression of the plates onto the spinous processes. In an exemplified aspect, the two planes are the coronal and axial planes.

As described, in one aspect, the implant defines an internal cavity in communication with its top and bottom portions. In another aspect, the method further comprises introducing bone graft material into the internal cavity, where the material is selected from the group consisting of autologous bone, allograft bone, bone substitute, and osteoinductive agent. In still another aspect, the method comprises introducing bone cement into the internal cavity.

In yet another exemplified aspect, the implantable device can comprise two spaced plates connected via a single post 520. In this aspect, an implant may or may not be present. In one aspect, the implantable device comprises first and second spaced plates 100, 200, the first plate 100 having a first surface 110 facing a second surface 210 of the second plate 200. In this aspect, the post 520 is connectable to the first and second plates. The post, in this aspect, has a first end portion 522, a second end portion 524, and a middle portion 526, where the first plate 100 is configured to connect to the first end portion 522 of the post 520 and the second plate 200 is configured to connect to the second end portion 524 of the post.

As with other aspects disclosed herein, in one aspect, the implantable device is configured for polyaxial movement of the first and second plates with respect to at least portions of the post 520 when the first and second plates are connected to the post. As with the other aspects described herein, the first and/or second plate can be configured to pivotally connect to a portion of the respective end portion of the post. Additionally, as described above, the first and second plates can be configured to connect to the post at a first and second connection point 530, 532, respectively. The connection points can be adjustable to control the distance between the first and second surfaces. In this aspect, the polyaxial movement of the plates with respect to the post can be accomplished in the various manners described herein above.

In one aspect, an implant 300, such as the ones described herein, can be positioned therebetween the first and second spaced place. In this aspect, at least a portion of the post is configured to pass therethrough a portion of the implant. In this aspect, the implant defines an aperture 380 through which the post can pass. The implant may also define an internal cavity (graft window) 370 for introduction of bone cement or bone graft material into the internal cavity to assist in fusion or bonding of the implant with the surrounding spinous processes.

In this aspect, the implantable device leads to a method of fixation of spinous processes of a subject. In one aspect, the method comprises assembling components into the described implant assembly, exposing a desired spinous process, connecting the first plate 100 to a portion of the first end portion 522 of the post, inserting the middle portion 526 of the post between adjacent spinous processes to position the post substantially between a first spinous process and a second spinous process, sliding the second plate 200 onto a portion of the second end portion 524 of the post 520 whereby portions of the first and second spinous processes are positioned in a space between the first and second surfaces, compressing the plates onto the first and second spinous processes; and maintaining compression of the plates onto the first and second spinous processes while affixing the first plate to the first end portion and the second plate to the second end portion.

This aspect of the method can also comprise angulating the first plate relative to the second plate in at least one plane during compression of the plates on the spinous processes. In an exemplified aspect, the step of angulating the first plate relative to the second plate comprises angulating the two plates in two planes during compression of the plates onto the spinous processes. In another aspect, the angulation of the first plate relative to the second plate is in coronal and axial planes. The method can also comprise means for pivotally connecting the first and second end portions, respectively.

In still another aspect, the implantable device can comprise the first and second spaced plates 100, 200 with a first post 120 having a first end 122 pivotally connected to the first surface 110 of the first plate 100 and a second end 124 spaced therefrom the first surface, as well as a second post 220 having a second end 222 pivotally connected to the second surface 210 of the second plate 200 and a first end 224 spaced therefrom the second surface. In this aspect, the second post is at least partially tubular, defining an interior longitudinal cavity 226. Additionally, in this aspect, at least a portion of the first post is configured to be telescopingly received by the interior longitudinal cavity. The position of the first post relative to the second post can be fixed using a set screw 228 positioned through a portion of the second post configured to engage the first post and maintain its position. The position may also be fixed using a collar or band around a portion of the second post that tightens in any known fashion. The second post may also be crimped onto the first post. Other known fixation means can also be employed.

As with the various aspects described herein, an implant can be positioned therebetween the first and second spaced plates. In this aspect, at least a portion of at least one of the first and second posts is configured to pass therethrough a portion of the implant.

In one exemplified aspect, the first plate 100 comprises a first socket 130 for complimentary receipt of the first end 122 of the first post 120, and the second plate 200 comprises a second socket 230 for complimentary receipt of the second end 222 of the second post 220. As with the other aspects described herein, there can be a first internal collar 140 within the first socket and a second internal collar 240 within the second socket. As such, the first collar is configured to engage a portion of the first end of the first post and the second collar is configured to engage a portion of the second end of the second post. In one aspect, each internal collar is configured to pivot within each respective socket, thereby permitting the polyaxial movement of the first and second plates with respect to the first and second posts, respectively. A first set screw can also be configured to interface with the first collar, and a second set screw can be configured to interface with the second collar to tighten the collars thereto the respective first and second posts.

As an alternative to the internal collars used for polyaxial movement, or in addition thereto, in one aspect, the first and second posts can be substantially flexible, thereby permitting the polyaxial movement of the first and second plates with respect to the respective first and second post.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An implantable device for fixation of spinous processes, comprising:
   a first plate having a first surface and defining an aperture, wherein the first plate further comprises a split ring collar positioned at least partially within the aperture and a moveable flange configured to engage the split ring collar;
   a second plate, spaced therefrom the first plate having a second surface facing the first surface, the second plate defining an aperture, wherein the second plate further comprises a second split ring collar positioned at least partially within the aperture and a second moveable flange configured to engage the second split ring collar; and
   a post configured to selectively pass through the split ring collar positioned within the aperture in the first plate and the second split ring collar positioned within the aperture in the second plate and connect the first plate to the second plate, wherein the connections of the first plate and the second plate to the post permit the first and second plates to move polyaxially with respect to one another and to translate along a longitudinal length of the post;
   wherein the first and second plates each comprise a set screw in communication with each moveable flange in the respective aperture, the set screw configured to move a portion of the respective moveable flange into engagement with a portion of the split ring collar to fix the position and orientation of the respective first and second plate to the post.

2. The implantable device of claim 1, further comprising an interbody cage positioned therebetween the first and second spaced plates, wherein at least a portion of the post is configured to pass therethrough a portion of the interbody cage.

3. The implantable device of claim 2, wherein a top portion of the interbody cage defines a longitudinal trough configured for complimentary receipt of a portion of a first spinous process.

4. The implantable device of claim 3, wherein a bottom portion of the interbody cage defines a longitudinal trough configured for complimentary receipt of a second spinous process, which is adjacent the first spinous process.

5. The implantable device of claim 3, wherein the longitudinal trough of the top portion has external edges that have a plurality of consecutive ridges configured for frictional engagement with a portion of the first spinous process.

6. The implantable device of claim 4, wherein the longitudinal troughs of the top and bottom portions have external edges that have pluralities of consecutive ridges configured for frictional engagement with a portion of the respective first and second spinous processes.

7. The implantable device of claim 2, wherein the interbody cage comprises a tapered distal nose.

8. The implantable device of claim 2, wherein the interbody cage has a top portion and an opposed bottom portion and defines an internal cavity in communication with at least one of the top portion and the bottom portion.

9. The implantable device of claim 2, wherein the interbody cage has a top portion and an opposed bottom portion and defines an internal cavity in communication with the top portion and the bottom portion.

10. A method of fixation of spinous processes of a subject comprising:
assembling components into an implant assembly comprising:
a first plate having a first surface and defining a first aperture, wherein the first plate further comprises a first split ring collar positioned at least partially within the first aperture and a first moveable flange configured to engage the first split ring collar;
a second plate, spaced therefrom the first plate having a second surface facing the first surface, the second plate defining a second aperture, wherein the second plate further comprises a second split ring collar positioned at least partially within the second aperture and a second moveable flange configured to engage the second split ring collar; and
a post having a first end portion, a second end portion, and a middle portion;
exposing a desired spinous process;
connecting the first plate to a portion of the first end portion of the post by inserting the first end of the post through the first aperture;
inserting the middle portion of the post between adjacent spinous processes to position the post substantially between a first spinous process and a second spinous process;
sliding the second plate onto a portion of the second end portion of the post by inserting the second end of the post through the second aperture whereby portions of the first and second spinous processes are positioned in a space between the first and second surfaces;
compressing the plates onto the first and second spinous processes; and
maintaining compression of the plates onto the first and second spinous processes while affixing the first plate to the first end portion by compressing the first flange onto the first split ring collar and the second plate to the second end portion by compressing the second flange onto the second split ring collar.

11. The method of claim 10, further comprising:
angulating the first plate relative to the second plate in at least one plane during compression of the plates on the spinous processes.

12. The method of claim 11, further comprising:
angulating the first plate relative to the second plate in two planes during compression of the plates onto the spinous processes.

13. The method of claim 12, wherein angulation of the first plate relative to the second plate is in coronal and axial planes.

14. The method of claim 10, wherein the first plate and the second plate are pivotally connected to the first and second end portions, respectively.

* * * * *